United States Patent [19]
Nacamulli et al.

[11] Patent Number: 5,527,710
[45] Date of Patent: Jun. 18, 1996

[54] RATE MEASUREMENTS OF BIOMOLECULAR REACTIONS USING ELECTROCHEMILUMINESCENCE

[75] Inventors: Laurette Nacamulli, Rockville; Jonathan K. Leland, Silver Spring; Stephanie A. Hayes, Gaithersburg, all of Md.

[73] Assignee: IGEN, Inc., Gaithersburg, Md.

[21] Appl. No.: 347,984

[22] Filed: Dec. 2, 1994

[51] Int. Cl.$^6$ .................................................. G01N 33/557
[52] U.S. Cl. ..................... 436/517; 436/149; 436/172; 436/501; 436/536; 436/537; 436/544; 436/546; 435/4; 435/6; 435/7.1; 435/7.5; 422/52; 422/82.01; 422/82.05; 422/82.08
[58] Field of Search ...................... 436/149, 172, 436/501, 517, 536, 537, 544, 546; 435/4, 6, 7.1, 7.5; 422/52, 82.01, 82.05, 82.08

[56] References Cited

U.S. PATENT DOCUMENTS 5,310,687  5/1994  Bard et al. ............................. 436/518

OTHER PUBLICATIONS

"Label–free Biosensor Technology Visualizes Biomolecular Interactions in Real Time", 8 No. 2, Products & Innovations Biosensors & Bioelectronics, xi–xiv.

Sjolander S. and Urbaniczky C., "Integrated Fluid Handling System for Biomolecular Interaction Analysis", 63 Analytical Chemistry 2338–2355 (1991).

Friguet et al., "Measurements of the True Affinity Constant in Solution of Antigen–Antibody Complexes by Enzyme–Linked Immunosorbent Assay", 77 Journal of Immunological Methods 305–319 (1985).

Primary Examiner—James C. Housel
Assistant Examiner—Rachel Heather Freed
Attorney, Agent, or Firm—William R. Robinson; John W. Ryan

[57] ABSTRACT

The rate of a biomolecular reaction, such as an enzymatic reaction or an affinity binding reaction, is measured using electrochemiluminescence ("ECL"). The reaction is conducted in an electrochemical cell with a mixture of reagents including a luminophore which will relate the concentration of a reactant, a reaction partner or the reaction product of a reaction partner to the ECL intensity. The reaction partner is a reagent which reacts with the reactant and which participates with the luminophore (or its reaction product participates with the luminophore) to cause the emission of ECL. The ECL intensity is modulated with a series of electrical pulses which are applied to the mixture of reagents at a preselected potential and for preselected intervals of time and duration. The ECL intensity is measured at the same intervals to provide a timed series of values (P). The same experiment is repeated except that the modulation is conducted after the reaction has gone to completion to obtain a timed series of values (C). The same experiment is repeated a third time in the absence of the reaction partner to obtain a times series of values (B). The results are normalized (N) using the following formula:

$$N = \frac{P-B}{C-B} \quad (I)$$

to obtain a series of values N which can be used to plot the time course (concentration vs. time) of the reaction.

36 Claims, No Drawings

RATE MEASUREMENTS OF BIOMOLECULAR REACTIONS USING ELECTROCHEMILUMINESCENCE

BACKGROUND OF THE INVENTION

1. Field of the Invention

The present invention relates to analytical methods and systems for measuring the rate of biomolecular reactions. More particularly, the invention has to do with the use of electrochemiluminescence ("ECL") to monitor in real time the progress of a biomolecular reaction. The method can be used to monitor the progress of affinity binding reactions and, as such, can be used in antibody-antigen binding rate measurements, among others. The method also can be used for the diagnostic determination of an enzyme activity or concentration and for other rate measurements as will be apparent to those skilled in the art.

2. Description of Related Art

There are various known methods for measuring the progress of biomolecular reactions and the present invention provides a new method of monitoring the rates of such reactions. The progress of enzymatic reactions, for example, has been monitored by spectrophotometry and fluorescence. These methods and others are used in modern laboratories and have been used by applicants to obtain reference data for the development of the new analytical technique of the present invention.

Antigen-antibody reaction rates can be measured using a technology called real-time biospecific interaction analysis which uses surface plasmon resonance to detect biomolecular interactions. The method was reported to be a valuable supplement to conventional methods of investigation in an article entitled "Label-Free Biosensor Technology Visualizes Biomolecular Interactions in Real Time", *Biosensors & Bioelectronics,* Vol. 8, No. 2, Products and Innovations, pp. xi–xiv. The use of surface plasmon resonance is also discussed by Sjolander, S. and Urbaniczky, C. in "Integrated Fluid Handling System for Biomolecular Interaction Analysis", *Analytical Chemistry* 1991, Vol. 63, pp. 2338–2345. According to the method, the kinetics for biomolecular interactions between an antigen and an antibody can be followed directly without labeling. The method is useful for detecting, in situ, low concentrations of biochemically active molecules having high molecular weight.

A general procedure for the determination of the dissociation constant ($K_D$) of antigen-antibody equilibria in solution is reported by Friguet, B., et al., in "Measurements of the True Affinity Constant in Solution of Antigen-Antibody Complexes by Enzyme-Linked Immunosorbent Assay", *Journal of Immunological Methods* 1985, Vol. 77, pp. 305–319. The method employs a classical indirect ELISA and is reported to permit the detection of very small concentrations of antibody and the determination of $K_D$ values as small as $10^{-9}$M.

The method and system of the present invention employ electrochemiluminescence which has been used heretofore in analytical methods for the qualitative and quantitative analysis of chemical moieties. In U.S. Pat. No. 5,310,687, for example, a chemical moiety is disclosed which comprises a chemical, biochemical or biological substance attached to one or more electrochemiluminescent organometallic compounds. Methods are disclosed for detecting low concentrations of the chemical moiety using chemiluminescent, electrochemiluminescent and photo-luminescent means. Compounds are disclosed which are useful for labeling substances of interest with ruthenium-containing and osmium-containing labels or other electrochemiluminescent labels. The labeled substances are useful in methods for detecting and quantifying analytes of interest in binding assays and competitive binding assays.

We have now discovered a method and system of employing electrochemiluminescence to monitor the progress of biomolecular reactions and the method can be employed in diagnostic kits for clinical use, research laboratories, and the like. The method employs commercially available equipment and provides a highly accurate means for diagnostic determination of an enzyme activity or concentration. The method also provides a means to measure antibody-antigen binding rates and it is useful for screening for high binding rate antibodies. In one embodiment, a method has been derived for measuring the rates of antibody binding to carcinoma embryonic antigen. In another embodiment, a method has been derived to determine lactate dehydrogenase for clinical applications.

SUMMARY OF THE INVENTION

A biomolecular reaction which is to be monitored according to the present invention must be carried out using a luminophore under reaction conditions which will relate the concentration of a reactant or a product of the reaction to the ECL intensity. The reagents employed in the reaction, therefore, will include a reaction partner which reacts with the reactant and participates with the luminophore to cause the emission of ECL. In some embodiments, it is the reaction product of the reaction partner which participates with the luminophore to cause the emission of ECL. The method of the invention also requires the modulation and measurement of the ECL intensity of the biomolecular reaction and the demodulation of the intensity measurement.

The biomolecular reaction is carried out in an electrochemical cell and a series of electrical pulses are applied at a preselected potential and at preselected constant intervals of time and constant duration to modulate the ECL output. The intensity of the resulting luminescence is measured at the same intervals to provide a timed series of values called reaction in progress (P). The same experiment is repeated, except that it is allowed to go to completion before ECL intensity is measured by pulsing and measuring luminescence under the same conditions to provide a timed series of values called reaction complete (C). The same experiment is repeated a third time in the absence of the reaction partner and the ECL intensity is measured at the same intervals to provide a timed series of values called blank (background reaction) (B).

The time course, concentration vs. time, of the reaction is determined by demodulating the intensity measurements. This is accomplished by subtracting the blank (B) from the reaction in progress (P) and dividing by the difference of the reaction complete (C) less the blank (B). Accordingly, the enzymatic reaction (P) is normalized (N) by the following formula:

$$N = \frac{P - B}{C - B} \tag{I}$$

The time course is compared to a known standard to determine concentration over time and the reaction rate can be determined at any point in time by taking the first derivative (tangential slope) at that point on the concentration vs. time curve.

The enzyme rate measurement method of the invention requires an enzymatic reaction which produces or consumes a substance which is ECL active. As the reaction progresses the ECL intensity will vary with the concentration of the ECL active substance. A luminophore and the ECL active substance (or the substance which produces the ECL active substance) are mixed with the other reactants. The enzyme is added last and the reaction is allowed to proceed in an electrochemical cell. A series of electrical pulses is applied, as explained above, and the ECL intensity is measured and demodulated to obtain the time course of the reaction.

In the measurement of binding reaction rates, for example, antibody-antigen binding rates, two reagents are prepared prior to the binding event. A luminophore, such as $Ru(2,2'$-bipyridine$)_3^{2+}$ (sometimes abbreviated herein as "$Ru(bpy)_3^{2+}$" the bipyridine ligand itself is sometimes abbreviated herein as "bpy"), is attached to the antibody whose binding rate is to be determined, and the antigen (the reaction partner) is attached to a magnetic bead. An ORIGEN® Analyzer available from Igen, Inc., 1530 East Jefferson Street, Rockville, Md. 20852, U.S.A., can be used to dispense samples containing the magnetic beads and conduct the analysis. The samples are drawn into the electrochemical flow cell of the Analyzer and the antigen coated magnetic beads are deposited uniformly onto the working electrode from the flow stream by placing the magnet directly below. The binding event is initiated and progressed by continuously drawing labeled antibody through the electrochemical flow cell of the analyzer. As the binding event proceeds the ECL active label binds to the magnetic bead. A series of electrical pulses are applied as described above. A rise in the ECL occurs as the binding proceeds and indicates reaction progress. The ECL intensity is then demodulated to obtain the time course of the reaction.

The electrochemiluminescent labels used according to the invention are sensitive, non hazardous and inexpensive, and they can be used in a wide variety of applications.

DESCRIPTION OF THE PREFERRED EMBODIMENTS

The time course of a biomolecular reaction is determined according to the present invention by forming a first reagent mixture containing a reactant, a luminophore and a reaction partner. The reactant reacts with the reaction partner, and the luminophore participates with the reaction partner to emit electrochemiluminescence upon exposure of the reagent mixture to electrical energy. In some embodiments of the invention, the reaction product of the reaction partner, rather than the reaction partner itself, participates with the luminophore to emit electrochemiluminescence. A series of electrical pulses is applied to the first reagent mixture at a preselected potential and at preselected intervals of time and duration, and the electrochemiluminescence is measured at the same intervals to obtain a value for each interval.

A second reagent mixture is formed which is the same as the first reagent mixture. The reagents of the second reagent mixture are allowed to react until the reaction is complete and then the mixture is exposed to a series of electrical pulses at the same potential, intervals of time and duration as was the first reagent mixture. The electrochemiluminescence also is measured at the same intervals as for the first reagent mixture to obtain a value for each interval.

A third reagent mixture is formed which is the same as the first reagent mixture except that it does not contain the reaction partner. A series of electrical pulses is applied to the third reagent mixture at the same potential, intervals of time and duration was the first reagent mixture. The electrochemiluminescence is measured at the same intervals as for the first reagent mixture to obtain a value for each interval.

The value obtained for the first interval for the third reagent mixture is subtracted from the value obtained for the first interval for the first reagent mixture to obtain a first difference. The value obtained for the first interval for the third reagent mixture also is subtracted from the value obtained for the first interval for the second reagent mixture to obtain a second difference. The first difference is divided by the second difference to obtain a normalized value for the first interval. The normalized value then is calculated in the same way for each successive interval to obtain a series of normalized values which can be plotted to illustrate the time course (concentration vs. time) graphically. Other mathematical operations can be performed on the data as will be apparent to those skilled in the art. For example, one can take the first derivative at any point on the normalized value curve to determine the rate of the reaction at that point.

The system of the invention comprises a first reagent mixture containing a reactant, a luminophore and a reaction partner. The reactant reacts with the reaction partner, and the luminophore participates with the reaction partner, or the reaction product of the reaction partner, to emit electrochemiluminescence upon exposure of the reagent mixture to electrical energy. The system further comprises a second reagent mixture which is the same as the first reagent mixture except that the reagents have been allowed to react and therefore it comprises reacted reagents. A third reagent mixture which is the same as the first reagent mixture except that it does not contain the reaction partner is also provided with the system. Finally, the system is provided with a means for separately exposing each of the first, second and third reagent mixtures to a series of electrical pulses at a preselected potential and at preselected intervals of time and duration, and a means for measuring the electrochemiluminescence at the same intervals.

The method of the invention is conducted in an apparatus provided with an electrode, such as an electrochemical cell. The biomolecular reaction which is monitored according to the invention is carried out in the apparatus using a luminophore under reaction conditions which will relate the concentration of a reactant, a reaction partner or the reaction product of the reaction partner to the ECL intensity, and the reaction partner is a reagent which reacts with the reactant and which participates (or its reaction product participates) with the luminophore to cause the emission of ECL.

The ECL intensity of the biomolecular reaction is modulated by means of an input potential applied to the electrode. The input potential induces the luminophore to emit a measurable ECL output by creating an excited state of the luminophore which luminesces at wavelengths between about 200 nanometers ("nm") and 900 nm at ambient temperatures. The input potential is incremented with time (e.g., the RAMP method), and the ECL output is detected as the response to the voltage change. The ECL peak occurs at the potential of the electrochemical reaction (peak potential) which is driven by the input potential.

Another way of generating ECL is by stepping the input voltage at or higher than the peak potential. The ECL then is observed as a sharp peak that decays with time.

According to the method of the invention a series of short pulses is applied to the electrode, also at a slightly higher voltage than the peak potential. The result is a series of ECL peaks corresponding to the individual voltage pulses. In this manner, a "sampling" of the ECL signal is obtained at constant intervals in time and the progression of a reaction with time can be followed. The intensity of this modulated ECL signal is measured at each time interval and the measurements are then demodulated to obtain the time course of the reaction.

The ECL reaction is slowed down by the method of the invention by using narrow voltage pulses and the decay rate due to the biomolecular reaction is compared to the decay rate due to the ECL reaction. (In an ECL reaction where no enzymatic reaction is going on, one long pulse at a high value will provide an ECL intensity which will decay over time.) In the time interval between pulses, new material diffuses to the electrode and is ready to react when the next voltage pulse comes, therefore each ECL peak is only slightly lower than the previous one.

Several parameters can be controlled such as the pulse potential and duration, the rest potential (i.e., the potential during the interval between pulses) and the time between each pulse as well as the concentration of the reactants to provide for better conditions for rate measurements for each particular biomolecular reaction, as will be apparent to those skilled in the art.

When the series of electrical pulses are applied at a preselected potential and at preselected constant intervals of time and constant duration to modulate the ECL output, the intensity of the resulting luminescence is measured at the same intervals to provide a timed series of values called reaction in progress (P). The same experiment is repeated, except that it is allowed to go to completion before ECL intensity is measured by pulsing and measuring luminescence under the same conditions to provide a timed series of values called reaction complete (C). The same experiment is repeated a third time in the absence of the reaction partner and the ECL intensity is measured at the same intervals to provide a timed series of values called blank (B).

The time course, concentration vs. time, of the reaction is determined by demodulating the intensity measurements. This is accomplished by subtracting the blank (B) from the reaction in progress (P) and dividing by the difference of the reaction complete (C) less the blank (B). Accordingly, the enzymatic reaction (P) is normalized (N) by the following formula:

$$N = \frac{P-B}{C-B} \qquad (1)$$

The time course is compared to a known standard to determine concentration over time and the reaction rate can be determined at any point in time by taking the first derivative (tangential slope) at that point on the concentration vs. time curve.

The method of the present invention as it applies to enzymatic reactions is generally suited to measuring the rate of oxido-reductase reactions. Oxido reductases catalyze oxidation reduction reactions and are classified in six categories as acting on

 (1)

 (2)

 (3)

 (4)

 (5)

and (6) NADH; NADPH.

The category of oxido reductases that is particularly suited to the method of the present invention is the dehydrogenases. As a group, dehydrogenases require for their activity a cofactor. A cofactor is a nonprotein component and it may be a metal ion or an organic molecule called a coenzyme. Suitable cofactors for dehydrogenases (as well as oxidases and other enzymes) are described in the literature and are well known in the art. Typical coenzymes for dehydrogenases are, for example, nicotinamide adenine dinucleotide (NADH) and nicotinamide adenine dinucleotide phosphate (NADPH).

Generally, a reaction catalyzed by a dehydrogenase, using NADH as an example, can be described as follows:

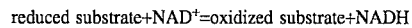

and the reaction may proceed in either direction. The substrate is the molecule on which the enzyme exerts catalytic action. Examples of reduced substrates include isocitrate, ethanol, lactate, malate, and glucose-6-phosphate.

In accordance with the enzyme rate measurement method of the present invention, substances (cofactors) are employed which are ECL active (i.e., the reaction partner) and which co-react with the reactant of an enzymatic reaction. Alternatively, the ECL active substance can be the reaction product of the reaction partner. As noted, above, the cofactors include NADH and NADPH and the respective oxidized forms thereof, $NAD^+$ and $NADP^+$, which are particularly suitable for use with dehydrogenases, and hydrogen peroxide ($H_2O_2$) which is particularly suitable for use with oxidases.

The enzymatic reaction must produce or consume the ECL active substance. As the process occurs, the substance is used for ECL, which relates the concentration of substances to the ECL intensity. For example, NADH produced in the following reaction is used to measure the enzyme reaction rate for glucose-6-phosphate dehydrogenase:

glucose-6-phosphate+$NAD^{30}$=6-phosphogluconate+NADH (1)

NADH+$Ru(bpy)_3^{2+}$=ECL (2)

wherein reaction (1) is carried out in the presence of glucose-6-phosphate dehydrogenases and $Ru(bpy)_3^{2+}$. As NADH is produced it reactions with $Ru(bpy)_3^{2+}$ according to reaction (2), when electrical pulses are applied, to produce ECL. The intensity of the ECL will increase with an increased rate of production of NADH and it will decrease with a decreased rate of production of NADH.

Alternatively, NADH consumed in the following reaction is used to measure the enzyme reaction rate for lactate dehydrogenase (LDH):

pyruvate+NADH=NAD$^+$+lactate  (3)

NADH+Ru(bpy)$_3$$^{2+}$=ECL  (4)

Wherein reaction (3) is carried out in the presence of LDH and Ru(bpy)$_3$$^{2+}$. As NADH is consumed it reacts less with Ru(bpy)$_3$$^{2+}$, according to reaction (4), when electrical pulses are applied, to produce ECL. The intensity of the ECL will decrease with an increased rate of consumption of NADH and it will increase with a decreased rate of consumption of NADH.

NADH is a particularly suitable coreactant for use in accordance with the enzyme rate measurement method of the present invention because it participates in numerous enzymatic reactions. The substrate is converted to products by the enzyme, and, in the process, NADH is converted to NAD$^+$ or vice versa depending upon the reaction. As NADH is produced (or consumed) it participates with the luminophore to yield ECL. The intensity of the light is proportional to the concentration of NADH at each time point. The change in NADH concentration is related to the activity of the enzyme catalyzing the reaction. The signal is plotted vs. time after point-by-point subtraction of the background and normalizing the signal of the luminophore with the initial (or final) concentration of NADH to obtain a time course.

The reaction mechanism between the Ru(bpy)$_3$$^{2+}$ and NADH as the coreactant that ultimately produces electrochemiluminescence involves a first step of oxidizing Ru(bpy)$_3$$^{2+}$ at the electrode according to (1) as follows:

Ru(bpy)$_3$$^{2+}$→Ru(bpy)$_3$$^{3+}$+e$^-$.  (1)

NADH is also oxidized at the electrode followed by a proton loss that produces the strong reducing agent, NAD radical according to (2) as follows:

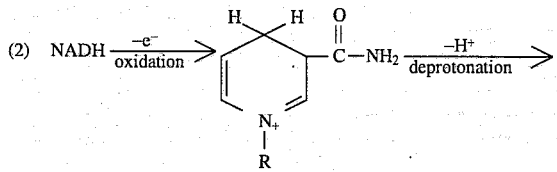

Next the NAD radical reacts with Ru(bpy)$_3$$^{3+}$ in a homogeneous reaction (3). The energy transfer is sufficient to raise the ruthenium complex to its excited state as follows:

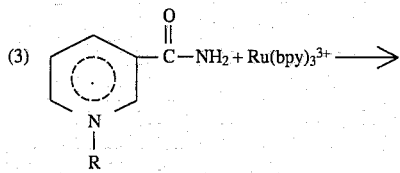

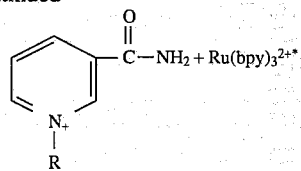

Upon decay to the ground state the tag molecule emits detectable light at 620 nm according to reaction (4) as follows:

Ru(bpy)$_3$$^{2+*}$→Ru(bpy)$_3$$^{2+}$+hv  (2)

The enzyme rate measurement method of the invention is conducted by mixing all of the reagents in a sample tube, and the enzyme is added last. Upon the addition of the enzyme, the sample is drawn into the electrochemical cell of an ORIGEN® Analyzer. A series of electrical pulses are applied at constant intervals of time and constant duration. (The ORIGEN® Analyzer generates a square wave, but triangle or sine waves also can be used.) The resulting luminescence from the luminophore is measured and indicates the amount of products formed as the enzymatic reaction progresses.

The method of the present invention as it applies to binding reactions can be used to monitor reactions such as those listed below:

antibody-antigen, such as CEA to anti-CEA;
ligand-receptor, such as a hormone binding to its receptor;
avidin-biotin;
base pairing, such as with DNA hybridization reactions;
lecitins-carbohydrates; and
enzyme-inhibitor.

In the measurement of binding reaction rates, two reagents are prepared prior to the binding event. When an antibody-antigen reaction is involved, for example, the luminophore is attached to the antibody (the antibody being the reactant) whose binding rate is to be determined, and the antigen (the reaction partner) is attached to a magnetic bead. The ORIGEN® Analyzer can be used to dispense samples containing the magnetic beads and conduct the analysis. The samples are drawn into the electrochemical flow cell of the Analyzer and the antigen coated magnetic beads are deposited uniformly onto the working electrode from the flow stream by placing the magnet directly below. The binding event is initiated and progressed by continuously drawing labeled antibody through the electrochemical flow cell of the analyzer. As the binding event proceeds the ECL active label binds to the magnetic bead. A series of electrical pulses are applied as described above. A rise in the ECL occurs as the binding proceeds and indicates reaction progress. The ECL intensity is then demodulated to obtain the time course of the reaction.

Luminophores which can be used in accordance with the present invention fall into two classes, namely, organic compounds and inorganic compounds. The organic compounds include fluorescent or phosphorescent polyaromatic hydrocarbons, such as rubrene, 9,10-diphenylanthracene, phthalocynanines, and phenanthrene. The inorganic compounds include fluorescent or phosphorescent transition metal chelates such as ruthenium tris-bipyridine, osmium tris-bipyridine, platinum diphosphonate, Mo$_6$Cl$_{12}$$^{2-}$; organometallic compounds; rare earth chelates such as terbium thenoyltrifluoroaectonate; europium dibenzoylmethide; and main group chelates such as silicon phthalocyanine. Particularly useful luminophores are Ru-containing and Os-containing compounds.

The luminophores which are disclosed in U.S. Pat. No. 5,310,687 can be used as luminophores according to the present invention and, among those disclosed, ruthenium complexes such as Ru(2,2'-bipyridine)$_3^{2+}$ are preferred.

The particular labels with which the present invention is concerned are electrochemiluminescent. They can often be excited to a luminescent state without their oxidation or reduction by exposing the compounds to electromagnetic radiation or to a chemical energy source such as that created by typical oxalate-$H_2O_2$ systems. In addition, luminescence of these compounds can be induced by electrochemical methods which do entail their oxidation and reduction. The method of the present invention has to do with exciting these labels with electrical pulses.

Extensive work has been reported on methods for detecting Ru(2,2'-bipyridine)$_3^{2+}$ using photoluminescent chemiluminescent, and electrochemiluminescent means: Rubenstein and Bard (1981), "Electrogenerated Chemiluminescence. 37. Aqueous Ecl Systems based on Ru(2,2'-bipyridine)$_2^{2+}$ and Oxalate or Organic Acids" J. Am. Chem. Soc. 103, pp 512–516; and White and Bard (1982), "Electrogenerated Chemilluminescence. 41. Electrogenerated Chemilluminescence and Chemilluminescence of the Ru(bpy)$_3^{2+}$— $S_2O_8^{2-}$— System in Acetonitrile-Water Solutions", 104 p 6891. This work demonstrates that bright orange chemiluminescence can be based on the aqueous reaction of chemically generated or electrogenerated Ru(bpy)$_3^{3+}$ with strong reductants produced as intermediates in the oxidation of oxalate ions or other organic acids. Luminescence also can be achieved in organic solvent $H_2O$ solutions by the reaction of electrogenerated, or chemically generated, Ru(bpy)$_3^{1+}$ with strong oxidants generated during reduction of peroxydisulfate. A third mechanism for production of electrochemiluminescence from Ru(bpy)$_3^{2+}$ involves the oscillation of an electrode potential between a potential sufficiently negative to produce Ru(bpy)$_3^{1+}$ and sufficiently positive to produce Ru(bpy)$_3^{3+}$. These three methods are called, respectively, "oxidative-reduction," "reductive-oxidation," and "the Ru(bpy)$_3^{3+/+}$ regenerative system".

The oxidative-reduction method can be performed in water, and produces an intense, efficient, stable luminescence, which is relatively insensitive to the presence of oxygen or impurities. This luminescence from Ru(bpy)$_3^{2+}$ depends upon the presence of oxalate or other organic acids such as pyruvate, lactate, malonate, tartrate and citrate, and means of oxidatively producing Ru(bpy)$_3^{3+}$ species. This oxidation can be performed chemically by such strong oxidants as PbO$_2$ or a Ce (IV) salt. It can be performed electrochemically by a sufficiently positive potential applied either continuously or intermittently. Suitable electrodes for the electrochemical oxidation of Ru(bpy)$_3^{3+}$ are, for example, Pt, purolytic graphite, and glassy carbon.

The reductive-oxidation method can be performed in partially aqueous solutions containing an organic cosolvent such as, for example, acetonitrile. This luminescence depends upon the presence of peroxydisulfate and a means of reductively producing an excited species. The reduction can be performed electrochemically by a sufficiently negative potential applied either continuously or intermittently. A suitable electrode for the electrochemical reduction of Ru(bpy)$_3^{2+}$ is for example, a polished glassy-carbon electrode.

The Ru(bpy)$_3^{3+/+}$ regenerative system can be performed in organic solvents such as acetonitrile or in partially aqueous systems, by pulsing an electrode potential between a potential sufficiently negative to reduce Ru(bpy)$_3^{2+}$ and a potential sufficiently positive to oxidize Ru(bpy)$_3^{2+}$. A suitable electrode for such a regenerative system is, for example, a Pt electrode. This system does not consume chemical reagents and can proceed, in principle, for an unlimited duration.

These three methods of producing luminescent Ru-containing compounds have in common the repetitive oxidation-reduction or reduction-oxidation of the Ru-containing compound. The luminescence of solutions containing these compounds is therefore highly dependent on the electric potential of the applied energy source, and is therefore highly diagnostic of the presence of the Ru-containing compound.

According to the present invention, a chemical moiety can be employed having the formula

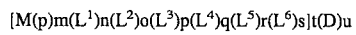
[M(p)m(L$^1$)n(L$^2$)o(L$^3$)p(L$^4$)q(L$^5$)r(L$^6$)s]t(D)u wherein M is ruthenium or osmium; P is a polydentate ligand of M; L$^1$, L$^2$, L$^3$, L$^4$, L$^5$ and L$^6$ are ligands of M, each of which may be the same as or different from each other ligand; D is a substance covalently bound to one or more of P, L$^1$, L$^2$, L$^3$, L$^4$, L$^5$ or L$^6$ through one or more amide or amine linkages; m is an integer equal to or greater than 1; each of n, o, p, q, r and s is zero or an integer; t is an integer equal to or greater than 1; u is an integer equal to or greater than 1; and P, L$^1$, L$^2$, L$^3$, L$^4$, L$^5$, L$^6$ and D are of such composition and number that the chemical moiety can be induced to emit electromagnetic radiation and the total number of bonds to M provided by the ligands of M equals the coordination number of M.

The invention also employs compounds which are particularly suitable as intermediates for attaching a luminescent ruthenium- or osmium-containing label to amino groups of chemical, biochemical and biological substances. These intermediates are thus particularly suitable for creating the chemical moieties employed according to the present invention. The intermediates are the mono- and di-N-hydroxysuccinimide esters of ruthenium or oxmium bis(2,2'-bipyridine) (2,2'-bipyridine-4,4'-dicarboxylic acid) and their salts; and ruthenium or osmium bis (2,2'-bipyridine) (4,4'-di(chloromethyl)-2,2'-bipyridine). These compounds may be synthesized by means known in the art.

The present invention also can employ the ruthenium-containing or osmium-containing chemical moieties in bonding methods for rate determinations involving analytes of interest.

(A)k(D)u wherein A is a compound which can be induced to repeatedly emit ECL by direct exposure to an electrochemical energy source; D is a substance such as a nucleotide, a polynucleotide, a serum-derived antibody or a monoclonal antibody (and other substances as described later in this specification) which is attached to A; k is an integer equal to or greater than 1, and u is an integer equal to or greater than 1 comprising a) forming a reagent mixture under suitable conditions containing the chemical moiety, and b) inducing the chemical moiety to repeatedly emit ECL by applying modulated electrical energy and then demodulating the ECL in accordance with the method of the present invention.

In one embodiment of the invention M is ruthenium. In another embodiment of the invention M is osmium.

The chemical moiety must have at least one polydentate ligand of M. If the moiety has greater than one polydentate ligand the polydentate ligands may be the same or different. Polydentate ligands include aromatic and aliphatic ligands. Suitable aromatic polydentate ligands include aromatic heterocyclic ligands. Preferred aromatic heterocyclic ligands are nitrogen-containing, such as, for example, bipyridyl, bipyrazyl, terpyridyl, phenanthrolyl and porphyrins.

Suitable polydentate ligands may be unsubstituted, or substituted by any of a large number of substituents known to the art. Suitable substituents include for example, alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, maleimide sulfur-containing groups, phosphorus containing groups, and the carboxylate ester of N-hydroxysuccinimide.

Additionally, at least one of $L^1$, $L^2$, $L^3$, $L^4$, $L^5$ and $L^6$ may be a polydentate aromatic heterocyclic ligand. Furthermore, at least one of these polydentate aromatic heterocyclic ligands may contain nitrogen. Suitable polydentate ligands include, but are not limited to, bipyridyl, bipyrazyl, terpyridyl, phenanthroyl, a porphyrin, substituted bipyridyl, substituted bipyrazyl, substituted terpyridyl, substituted phenanthroyl or a substituted porphyrin. These substituted polydentate ligands may be substituted with an alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, maleimide, a sulfur-containing group, a phosphorus-containing group or the carboxylate ester of N-hydroxysuccinimide.

The chemical moiety can contain two bidentate ligands, each of which is bipyridyl, bipryazyl, terpyridyl, phenanthrolyl, substituted bipyridyl, substituted bipyrazyl, substituted terpyridyl or substituted phenanthrolyl.

Alternatively, the chemical moiety can contain three bidentate ligands, each of which is bipyridyl, bipyrazyl, terpyridyl, phenanthrolyl, substituted bipyridyl, substituted bipyrazyl, substituted terpyridyl or substituted phenanthrolyl. The chemical moiety may comprise ruthenium. In another embodiment of the invention, the chemical moiety comprises ruthenium, two bidentate bipyridyl ligands and one substituted bidentate bipyridyl ligand.

In still another embodiment the chemical moiety can contain a tetradentate ligand such as a porphyrin or substituted porphytin.

The chemical moiety may have one or more monodentate ligands, a wide variety of which are known to the art. Suitable monodentate ligands include, for example, carbon monoxide, cyanides, isocyanides, halides, and aliphatic, aromatic and heterocyclic phosphines, amines, stibines, and arsines.

Particularly preferred embodiments of the chemical moiety comprise bis(2,2'-bipyridyl) ruthenium(II) and tris(2,2'-bipyridyl) ruthenium(II).

One or more of the ligands of M can be attached to additional chemical labels, such as, for example, radioactive isotopes, fluorescent components, or additional luminescent ruthenium- or osmium-containing centers.

Suitable substances (D) include many biological substances, for example, whole cells, viruses, subcellular particles, proteins, lipoproteins, glycoproteins, peptides, nucleic acids, polysaccharides, lipopolysaccharides, lipids, fatty acids, cellular metabolites, hormones, pharmacological agents, tranquilizers, barbituates, alkaloids, steroids, vitamins, amino acids and sugars. Whole cells may be animal, plant or bacterial, and may be viable or dead. Examples include plant pathogens such as fungi and nematodes.

Within this application the term "subcellular particles" means subcellular organelles, membrane particles as from disrupted cells, fragments of cell walls, ribosomes, multienzyme complexes, and other particles which can be derived from living organisms. Also, within this application, nucleic acids means chromosomal RNA, plasmid RNA, viral RNA and recombinant INA derived from multiple sources. Nucleic acids also include RiAs, for example messenger RiAs, ribosomal IRNAs and transfer RNAS. Polypeptides include, for example, enzymes, transport proteins, receptor proteins and structural proteins such as viral coat proteins. Preferred polypeptides are enzymes and serum-derived antibodies. Particularly preferred polypeptides are monoclonal antibodies. Hormones include, for example, insulin and T4 thyroid hormone. Pharmacological agents include, for example, cardiac glycosides. It is also within the scope of this invention to include synthetic substances which chemically resemble biological materials, such as synthetic peptides, synthetic nucleic acids, and synthetic membranes, vesicles and liposomes. The foregoing is not intended to be a comprehensive list of the biological substances suitable for use in this invention, but is meant only to illustrate the wide scope of the invention.

Biological and nonbiological substances (D) are covalently bound to a ligand of M through one or more amide or amine linkages. In the case of amide linkages, the linkages may be oriented so that material (D) is bonded directly either to the carbonyl or to the nitrogen of the amide linkage. These chemical moieties may be ionized. If so, it is understood in the art that many different counterions will serve to neutralize the charge of preparations of the chemical moiety. Suitable cations include for example $H^+$, $NH_4^+$, guanidinium $Ag^+$, $Li^+$, $N^+$, $K^+$, $Mg^{2+}$, and $Mn^{2+}$. Suitable anions include, for example, halides, $OH^-$, carbonate, $SO_4^{2-}$, hexafluorophosphate and tetrafluoroborate.

The chemical moieties also are particularly suitable as intermediates for attaching a luminescent ruthenium-containing or osmium-containing label to amino groups of chemical, biochemical and biological substances. These intermediates are thus particularly suitable for synthesizing chemical moieties according to the present invention. The intermediates are the mono- and di-N-hydroxysuccinimide esters of ruthenium and osmium 4,4'-(dicarboxy)- 2,2'-bipyridyl, bis(2,2'-bipyridyl) and their salts; and ruthenium and osmium 4,4'-(dichloromethyl)-2,2'-bipyridyl, bis(2,2' bipyridyl) and their salts.

The chemical structures of these intermediates and methods of preparing them are set forth in the U.S. Pat. No. 5,310,687 referenced above.

A preferred method of synthesizing the ruthenium-containing N-hydroxysuccinimide esters is to first react ruthenium dichloro-bis (2,2'-bipyridine) with 2,2'-bipyridine-4, 4'-dicarboxylic acid in a hot aqueous methanol solution of sodium bicarbonate. After acidification, an aqueous solution of $NAPF_6$ is added to the solution of carboxylated ruthenium compound. The isolated hexafluorophosphate salt of the ruthenium complex is then esterified by reaction with N-hydroxysuccinimide in the presence of dicyclohexylcarbodiimide in dimethylformamide. Of course, many variations on the structure of the N-hydroxysuccinimide component are possible without substantially altering the usefulness of the intermediates.

The intermediates may be ionized. If so, it is understood in the art that many different counterions will serve to neutralize the charge of preparations of the intermediate and form a salt. Suitable cations for forming these salts include for example $NH_4^+$, guandinium, $Ag^+$, $Li^+$, $Na^+$, $K^+$, $Ca^{2+}$, $Mg^{2+}$, and $Cd^{2+}$. Suitable anions for forming these salts include, for example, halides, carbonate, $SO_4^{2-}$, hexafluorophosphate, and tetrafluoroborate.

The intermediates are useful for labeling substances containing a free amino group capable of attacking the carboxylate ester, and thereby displacing N-hydroxysuccinimide, or of attaching the chloromethyl group, and thereby displacing chloride.

Applicants' experience with $Ru(bpy)_3^{2+}$-labeled substances indicates the advantages of using ruthenium-containing and osmium-containing compounds as chemical labels. They are stable for long periods and may be attached efficiently to a wide variety of chemical, biochemical and biological materials. The labels are safe and relatively inexpensive. They give a highly characteristic signal and do not occur in nature. Measurements based on luminescence of the labels are sensitive, fast and reproducible. There is very little interference with detection based on luminescence of these labels by such components as phosphate buffered saline, Tween® (a surfactant), liver tissue extract or serum. Luminescence-based measurement of these labels does not destroy the sample or labeled materials and may be performed repetitively. The signal is generated repeatedly by each molecule of label, thereby enhancing the sensitivity with which these labels may be detected.

Suitable conditions for forming the reagent mixture will be known to those skilled in the art and will depend on the type of reagent mixture involved. For example, suitable conditions for an aqueous reagent mixture may include appropriate concentrations of chemical moiety and other reagents such as oxidants, pH, salt concentration and the like. For a solid sample, suitable conditions for forming a reagent mixture may include addition of a conducting liquid.

The present invention can employ osmium-containing moieties as well as ruthenium-containing moieties and the wide variety of luminescent moieties which can be made by varying the chemical structure of the ligands. Each of these variations in the metal and the ligands can change the precise value of the energy input required to create the luminescent excited state. Similarly, the wavelength of the emitted electromagnetic radiation will be dependent upon the nature and environment of the ruthenium-containing or osmium-containing material. Generally, photoluminescence excitation and emission will occur with electromagnetic radiation of between about 200 nanometers and about 900 nanometers in wavelength. Chemiluminescent and electrochemiluminescent emission will generally occur with the emitted electromagnetic radiation being between about 200 nanometers and about 900 nanometers in wavelength. The potential at which the reduction or oxidation of the chemical moiety will occur depends upon its exact chemical structure as well as factors such as the pH of the solution and the nature of the electrode used. Generally, it is well known in the art how to determine the optimal emission and excitation wavelengths in a photoluminescent system, and the optimal potential and emission wavelength of an electrochemiluminescent and chemiluminescent system.

EXAMPLES

An ORIGEN® Analyzer was used in the following experimental work. The regular operation of the instrument is configured for detecting one ECL result per sample prior to the flushing of that sample to waste. We modified the regular operation so that each tube could be analyzed individually. That is, the contents of each tube were drawn into the cell and allowed to remain there while a series of pulses was applied to the sample. Each pulse provided a data point so that a series of data points was obtained for each sample.

Typically, in the case of enzymatic reactions, the first sample to be run (reaction in progress) contained the $Ru(bpy)_3^{2+}$ molecule and all the reagents for the enzymatic reaction except for the enzyme. The tube was loaded on to the carousel of the Analyzer and the Analyzer was started. (The surface of the electrode was cleaned prior to operation.)

The sample mixture, still in the tube, was vortexed. At this point the Analyzer was programmed to stop and alert the operator to pipet in the enzyme. Once this was performed, operation of the Analyzer was resumed with the instantaneous recording of the time in seconds. With each voltage pulse generating an ECL output, a time stamp was provided. In this manner, a time course of the ECL signal was obtained.

After all the data was collected for the first tube, a second sample tube that contained the same composition as the first one followed. Except in this case the enzyme had been allowed the time to act and the reaction had reached completion. The sample was then subjected to the same voltage scheme. The results from the first tube were normalized to the results from the second tube which was the ECL output (or ECL decay) only. (Alternatively, a tube that contains NADH and $Ru(bpy)_3^{2+}$ at the same concentrations as the first tube can be assayed for this purpose.)

A third tube was also run which contained everything except the substrate, for background purposes. The ECL results from this tube were subtracted from both the in-progress tube and the completed one, prior to the numerical normalization, point by point.

The instrument sampled at a rate of one data point per 10 milliseconds ("msec"). Therefore a pulse that was 100 msec long, for example, would yield 10 samplings during that period.

A similar experimental protocol was followed for antibody-antigen rate measurements as explained in more detail below.

Example 1

Enzymatic Reaction Where NADH is Generated

Glucose-6-phosphate dehydrogenase ("G-6-PDH") catalyses the oxidation of glucose-6-phosphate to 6-phosphogluconate with $NAD^+$ as a coreactant that is reduced to NADH. The reaction is as follows:

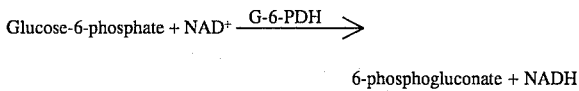

6-phosphogluconate + NADH

The experiment was carried out in 50 mM phosphate buffer at pH 7.5. A pH of 7.0–7.5 can be used and a carbonate buffer can be used instead of phosphate. The solution contained 0.53 g/L Triton X-100. The buffer was used both as the assay buffer and incubation buffer for the sample. The concentration of luminophore was 1E-4M $Ru(bpy)_3^{2+}$ and typical concentrations for the luminophore can be from about 1E-6M to about 1E-4M.

The sample was drawn from the tube into the electrochemical cell of the ORIGEN®Analyzer at the time recorded as zero. While in the cell compartment, the electrode was subject to a series of pulses from zero to 1800 millivolts ("mV") versus Ag/AgCl. The pulse duration was 460 milliseconds ("msec") and the rest potential was zero for 250 msec. Typical pulse rates can be from about 100 to about 500 milliseconds. The number of pulses was 20, and the number can be from about 10 to about 40.

The kinetics of the reaction were followed by monitoring the ECL output with time as NADH was generated and reacted with $Ru(bpy)_3^{2+}$. The reaction reached about 50% of completion after about 7 minutes.

The experiment was repeated under the same conditions except that the reaction was allowed to go to completion before ECL intensity was measured.

The experiment again was repeated under the same conditions except that $NAD^+$ was not added to the reaction mixture.

A fourth experiment was run using the same reactants as the first run in this example except that the reaction was analyzed using a spectrophotometer. The reaction reached about 50% of completion after about 7 minutes. The spectrophotometric results were compared with the normalized curve for the method of the invention and they correlated well.

Example 2

The Inhibition Effect of the Phosphoric Group

The experiments of Example 1 were repeated except that the concentration of phosphate buffer was varied to demonstrate the inhibition effect of the phosphoric group. The results expressed in the time it takes to convert half the amount of substrate into products ("t½") are summarized in the following table:

| Phosphate buffer concentration (mM) | t½ from spectrophotometer (min.) | t½ from electrochemiluminescence (min.) |
|---|---|---|
| 50 | 1.33 | 1.37 |
| 100 | 2.36 | 2.30 |
| 150 | — | 4.73 |
| 200 | 7.20 | 7.03 |

As the concentration of the buffer was increased, t½ was increased, marking a slow down in the kinetics. The results from the two methods agreed well.

Example 3

Enzymatic Reaction Where NADH is Consumed

Lactate dehydrogenase ("LDH") catalyses the conversion of pyruvate to lactate with NADH as a coreactant which is consumed to form the oxidized form $NAD^+$ as follows:

Pyruvate + NADH $\xrightarrow{LDH}$ Lactate + $NAD^+$

The NADH was present in a concentration of $10^{-2}$M, with $10^{-4}$M $Ru(bpy)_3^{2+}$, and the same experimental protocol as was followed in Example 1 was repeated here. The electrode was pulsed twenty times at 1800 mV for 460 msec and the rest potential was zero for 250 msec. The total time course was a little over 3000 msec. The normalized results compared well with the spectrophotometric analysis.

As this reaction progresses there is less NADH to react with $Ru(bpy)_3^{2+}$ and the ECL signal goes down gradually. However due to the nature of the ECL decay, the two reactions are in competition. The decay from the overall reaction appears to be faster compared to the absorbance data because there is less NADH substrate with each pulse.

It would be instrumental if the rate of the ECL decay was reduced so that the net effect measured would be due to the enzymatic reaction. To that effect the parameters of the pulse and the concentrations of NADH and $Ru(bpy)_3^{2+}$ were selected to provide a more stable ECL signal. The result was a very steady ECL output over a period of three minutes.

The normal clinical range of LDH in serum is 100 to 200 U/L, which is equivalent to 1 to 2 nM of the enzyme, from calculation based on the activity of the enzyme. These values are right in the range assayed and, accordingly, the test can be used to determine LDH for clinical applications.

Example 4

Streptavidin—Biotinylated DNA

The method of measurement is very similar to that used to measure NADH and enzyme kinetic reactions as discussed above. In the NADH/enzymatic experiments, the reaction rate is very fast, therefore, the sample must be quickly aspirated just before the run begins. However, for the antibody-antigen measurements, a much longer reaction time is anticipated and the experiment must be set up slightly different.

The software program which controls the ORIGEN® Analyzer was modified so that a continuous flow of antibody could be drawn across the antigen labeled beads at the electrode surface. The instrument was programmed to run the reaction from a two tube set up. The antigen-labeled beads were drawn from a first tube and captured on the electrode with the magnet. The carousel was incremented and the antibody label solution (which was in substantial excess in terms of concentration) was drawn from the second tube across the beads at the electrode surface and the binding reaction began.

Similar to the NADH/enzyme kinetic method, it was decided to use a pulse variation of the step potential voltage waveform in these experiments such that multiple pulses were generated over an extended time interval with a clock timer incorporated to keep track of the elapsed time after each pulse was generated.

When using the repetitive pulse waveform, several parameters can be optimized for the particular reaction to be measured and these can easily be determined by those skilled in the art on the basis of the guidance provided by the present specification. The parameters include the number of pulses, the pulse width, the delay time between pulses, the step potential voltage and the rest potential.

The method of measurement was very similar to that used to measure NADH and enzymatic kinetic reactions. Three separate reactions were run, and each employed two tubes as noted above. In preparation for the experiment, we coated 280 magnetic beads with streptavidin, added them to a first tube and then added a biotinylated DNA label. A biotinylated DNA labeled calibrator was added to a second tube.

Using the terms defined in this specification, the reactions were conducted as described below:

Reaction-in-progress—Once the measurement cycle began the concentration changed over time as binding occurred and the reaction completed.

Tube 1: Streptavidin coated beads

Tube 2: Biotinylated DNA labeled calibrator

Reaction-complete—The reaction was previously allowed to go to completion, so the intensity measurements were a result of the ECL decay only.

Tube 1: Streptavidin coated beads combined with biotinylated DNA label and allowed to bind completely.

Tube 2: Biotinylated DNA labeled calibrator.

Background reaction—There were no beads present, therefore the signal generated was a result of the label (background) only.

Tube 1: Assay Buffer (no beads present for binding).

Tube 2: Biotinylated DNA labeled calibrator.

After the three reactions were run, the normalized reaction curve was obtained using the formula:

$$N = \frac{P-B}{C-B} \quad (I)$$

as explained above. A tube-to-tube time course was then run using twenty tubes of beads and label at the same concentrations used above. They were pipetted and the run was immediately started. Therefore, the binding reaction took place in each tube, and the time of completion could be determined when the curve (ECL intensity vs. time) began to plateau. According to this time course, the reaction was completed in around 6 minutes. This was a much faster completion time than that obtained by the 3-step time course method.

At this point it was suspected that the streptavidin-biotin reaction was diffusion limited when using the 3-step method. To lend more support to this conclusion, a half-life study was performed using the 3-step time course method.

The 3-step time course method was repeated using 6 different concentrations of beads: 20 ug, 4 ug, 2 ug, 1.3 ug, 1.0 ug, and 0.8 ug (per 300 uL). As would be expected, as the bead concentration was decreased the reaction completed much faster.

Subsequently, the half-life of each concentration was obtained. Since the label was in substantial excess, the reaction was pushed to follow pseudo-first order kinetics. In a first order reaction, the half-life ("t½") is independent of concentration and is defined as:

$$t\textonehalf = 0.693/k$$

where k is the binding constant. Therefore, the half-life should be constant regardless of concentration if the reaction is first order. In a plot of bead concentration versus half life, where the t½ value was taken at 0.5 minutes, assuming that all of the normalized reactions should plateau at a relative value of 1.0, the half-life steadily decreased as the concentration decreased. The results are summarized below:

| bead concentration (ug.) | half-life (minutes) |
|---|---|
| 0.8 | 7.5 |
| 1.0 | 8 |
| 1.3 | 10 |
| 2 | 12 |
| 4 | 16 |
| 20 | 35 |

This steady decrease in the t½ value is an indication that the streptavidin-biotin system is mass transfer limited at the electrode surface. This explains why the reaction took much longer to complete when using the 3-step method versus the tube-to-tube method.

Although the streptavidin-biotin reaction was diffusion limited, the ECL 3-step time course measurement method should be feasible on a system in which the binding rates are significantly slower and therefore not diffusion limited.

Example 5

The CEA Antibody-Antigen System

The CEA assay format used in these experiments consisted of streptavidin-coated beads bound to a biotinylated CEA antigen which is subsequently bound to a labeled CEA specific antibody. The reaction rate being measured in this system is not the streptavidin-biotin reaction but the CEA antibody-antigen reaction.

A CEA antibody referred to as 1F3 was obtained, and the ECL 3-step time course method was attempted on this system to be compared with values previously obtained on the BIAcore system using the same 1F3 antibody. (The BIAcore system employs surface plasmon resonance and it is available from Pharmacia Biosensor AB.)

The highest concentration of 1F3 label chosen to run using the 3-step method was 11 nM, which is comparable in concentration to the 10 nM low end concentration run on the BIAcore. In addition, two lower concentrations of 5.5 nM and 2.7 nM were run. The normalized profile obtained from the 11 nM 1F3 label solution had the desired shape, however it was very noisy. This is because in using the ECL method as described, both the label which binds to the beads, and the free label which does not bind (which is considered background signal) are simultaneously present at the electrode surface. At high concentrations of label, it becomes difficult to discriminate between the bound and the unbound phases, hence a smooth normalized reaction profile cannot be obtained. The normalized profiles for the 5.5 nM and 2.7 nM concentrations of 1F3 antibody were much smoother, which again supports how the contribution of the unbound label at the electrode can affect the amount of noise in the signal. Since the concentration of unbound label present at the electrode is less, it is much easier to discriminate the bound phase signal and a much smoother profile is obtained.

On the BIAcore system, a series of 1F3 label concentrations, ranging from 10 nM to 500 nM were run. The current 3-step method on the ECL system does not allow for label concentrations much higher than 10 nM.

To obtain a comparison of the ECL 3-step method to the BIAcore method, a mathematical analysis was performed on the data obtained for the three normalized concentration curves to derive the experimental association rate constant, $k_a$. The $k_a$ value for the data obtained on the BIAcore was $4.0 \times 10^5 M^{-1} sec^{-1}$. For the ECL data a mean ($\pm$SD)$k_a$ value of $9.0 \times 10^5$ ($\pm 4.7 \times 10^5$) $M^{-1} sec^{-1}$ was obtained. This value is an average of the three $k_a$ values for each concentration.

What is claimed is:

1. A method of determining the time course of a biomolecular reaction comprising (a) forming a first reagent mixture containing a reactant, a luminophore and a biomolecular reaction partner wherein the reactant reacts with the biomolecular reaction partner, and the luminophore participates with the biomolecular reaction partner, or a reaction product of the biomolecular reaction partner, to emit electrochemiluminescence upon exposure of the reagent mixture to electrical energy;

(b) exposing the first reagent mixture to a series of electrical pulses at a preselected potential and at preselected intervals of time and duration, and measuring the electrochemiluminescence at the preselected intervals of time to obtain a value for each interval;

(c) forming a second reagent mixture having the components contained in the first reagent mixture;

(d) allowing the second reagent mixture to react until the reaction is complete and then exposing the mixture to a series of electrical pulses at the preselected potential, intervals of time and duration as performed in step (b) and measuring the electrochemiluminescence at the preselected intervals of time as performed in step (b) to obtain a value for each interval;

(e) forming a third reagent mixture having the components contained in the first reagent mixture except that it does not contain the biomolecular reaction partner;

(f) exposing the third reagent mixture to a series of electrical pulses at the preselected potential, intervals of time and duration as performed in step (b) and measuring the electrochemiluminescence at the preselected intervals of time as performed in step (b) to obtain a value for each interval;

(g) subtracting the value obtained for the first interval in step (f) from the value obtained for the first interval in step (b) to obtain a first difference;

(h) subtracting the value obtained for the first interval in step (f) from the value obtained for the first interval in step (d) to obtain a second difference;

(i) dividing the first difference by the second difference to obtain a normalized value for the first interval;

(j) repeating steps (g), (h) and (i) for each successive interval to obtain a normalized value for each successive interval;

(k) and determining the time course of the biomolecular reaction from the normalized value of all of the intervals.

2. The method of claim 1 wherein the reactant and the luminophore are combined in a chemical moiety having the formula

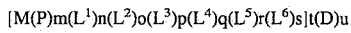

wherein M is ruthenium or osmium; P is a polydentate ligand of M; $L^1, L^2, L^3, L^4, L^5$ and $L^6$ are ligands of M, each of which may be the same as or different from each other ligand; D is a substance covalently bound to one or more of P, $L^1, L^2, L^3, L^4, L^5$ or $L^6$ through one or more amide or amine linkages; m is an integer equal to or greater than 1; each of n, o, p, q, r and s is zero or an integer; t is an integer equal to or greater than 1; u is an integer equal to or greater than 1; and P, $L^1, L^2, L^3, L^4, L^5, L^6$ and D are of such composition and number that the chemical moiety can be induced to emit electromagnetic radiation and the total number of bonds to M provided by the ligands of M equals the coordination number of M.

3. The method of claim 1 wherein the luminophore is selected from the group consisting of fluorescent or phosphorescent polyaromatic hydrocarbons and fluorescent or phosphorescent transition metal chelates.

4. The method of claim 3 wherein the transition metal chelates are organometallic compounds.

5. The method of claim 1 wherein the luminophore is selected from the group consisting of Ru-containing and Os-containing compounds.

6. The method of claim 1 wherein the luminophore is ruthenium tris-bypyridine or osmium tris-bipyridine.

7. The method of claim 1 wherein the biomolecular reaction is an enzymatic reaction, the reagent mixture contains an enzyme and the reactant is a substrate on which the enzyme exerts catalytic action, and the biomolecular reaction partner is a cofactor.

8. The method of claim 7 wherein the luminophore is selected from the group consisting of fluorescent or phosphorescent polyaromatic hydrocarbons and fluorescent or phosphorescent transition metal chelates.

9. The method of claim 7 wherein the enzyme is an oxido reductase.

10. The method of claim 9 wherein the oxido reductase is a dehydrogenase.

11. The method of claim 7 wherein the cofactor is a metal ion.

12. The method of claim 7 wherein the cofactor is a coenzyme.

13. The method of claim 12 wherein the coenzyme is in its oxidized form.

14. The method of claim 1 wherein the biomolecular reaction is a binding reaction.

15. The method of claim 14 wherein the binding reaction is selected from the group consisting of antibody-antigen, ligand-receptor, avidin-biotin, base pairing, lectin-carbohydrate, and enzyme-inhibitor.

16. The method of claim 14 wherein the luminophore is selected from the group consisting of fluorescent or phosphorescent polyaromatic hydrocarbons and fluorescent or phosphorescent transition metal chelates.

17. The method of claim 14 wherein the reactant and the luminophore are combined in a chemical moiety having the formula

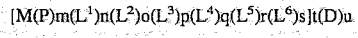

wherein M is ruthenium or osmium; P is a polydentate ligand of M; $L^1, L^2, L^3, L^4, L^5$ and $L^6$ are ligands of M each of which may be the same as or different from each other ligand; D is a substance covalently bound to one or more of P, $L^1, L^2, L^3, L^4, L^5$ or $L^6$ through one or more amide or amine linkages; m is an integer equal to or greater than 1; each of n, o, p, q, r and s is zero or an integer; t is an integer equal to or greater than 1; u is an integer equal to or greater than 1; and P, $L^1, L^2, L^3, L^4, L^5, L^6$ and D are of such composition and number that the chemical moiety can be induced to emit electromagnetic radiation and the total number of bonds to M provided by the ligands of M equals the coordination number of M.

18. A method of determining the time course of an enzymatic reaction comprising (a) forming a first reagent mixture containing an enzyme, a reactant on which the enzyme exerts catalytic action, a luminophore and a reaction partner which is a cofactor wherein the reactant reacts with the reaction partner, and the luminophore participates with the reaction partner, or a reaction product of the reaction partner, to emit electrochemiluminescence upon exposure of the reagent mixture to electrical energy;

(b) exposing the first reagent mixture to a series of electrical pulses at a preselected potential and at preselected intervals of time and duration, and measuring the electrochemiluminescence at the preselected intervals of time to obtain a value for each interval;

(c) forming a second reagent mixture having the components contained in the first reagent mixture;

(d) allowing the second reagent mixture to react until the reaction is complete and then exposing the mixture to a series c. electrical pulses at the preselected potential, intervals of time and duration as performed in step (b) and measuring the electrochemiluminescence at the preselected intervals of time as performed in step (b) to obtain a value for each interval;

(e) forming a third reagent mixture having the components contained in the first reagent mixture except that it does not contain the reaction partner;

(f) exposing the third reagent mixture to a series of electrical pulses at the preselected potential, intervals of time and duration as performed in step (b) and measuring the electrochemiluminescence at the preselected intervals of time as performed in step (b) to obtain a value for each interval;

(g) subtracting the value obtained for the first interval in step (f) from the value obtained for the first interval in step (b) to obtain a first difference;

(h) subtracting the value obtained for the first interval in step (f) from the value obtained for the first interval in step (d) to obtain a second difference;

(i) dividing the first difference by the second difference to obtain a normalized value for the first interval;

(j) repeating steps (g), (h) and (i) for each successive interval to obtain a normalized value for each successive interval;

(k) and determining the time course of the enzymatic reaction from the normalized value of all of the intervals.

19. The method of claim 18 wherein the luminophore is selected from the group consisting of fluorescent or phosphorescent polyaromatic hydrocarbons and fluorescent or phosphorescent transition metal chelates.

20. The method of claim 18 wherein the enzyme is an oxido reductase.

21. A method of determining the time course of a binding reaction comprising (a) forming a first reagent mixture containing a reactant, a reaction partner and a luminophore, wherein the reactant reacts with the reaction partner in a reaction selected from the group consisting of antibody-antigen, ligand-receptor, avidin-biotin, base pairing, lectin-carbohydrate, and enzyme-inhibitor, and the luminophore participates with the reaction partner to emit electrochemiluminescence upon exposure of the reagent mixture to electrical energy;

(b) exposing the first reagent mixture to a series of electrical pulses at a preselected potential and at preselected intervals of time and duration, and measuring the electrochemiluminescence at the preselected intervals of time to obtain a value for each interval;

(c) forming a second reagent mixture having the components contained in the first reagent mixture;

(d) allowing the second reagent mixture to react until the reaction is complete and then exposing the mixture to a series of electrical pulses at the preselected potential, intervals of time and duration as performed in step (b) and measuring the electrochemiluminescence at the preselected intervals of time as performed in step (b) to obtain a value for each interval;

(e) forming a third reagent mixture having the components contained in the first reagent mixture except that it does not contain the reaction partner;

(f) exposing the third reagent mixture to a series of electrical pulses at the preselected potential, intervals of time and duration as performed in step (b) and measuring the electrochemiluminescence at the preselected intervals of time as performed in step (b) to obtain a value for each interval;

(g) subtracting the value obtained for the first interval in step (f) from the value obtained for the first interval in step (b) to obtain a first difference;

(h) subtracting the value obtained for the first interval in step (f) from the value obtained for the first interval in step (d) to obtain a second difference;

(i) dividing the first difference by the second difference to obtain a normalized value for the first interval;

(j) repeating steps (g), (h) and (i) for each successive interval to obtain a normalized value for each successive interval;

(k) and determining the time course of the binding reaction from the normalized value of all of the intervals.

22. The method of claim 21 wherein the reactant is attached to the luminophore to form a chemical moiety having the formula

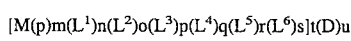

$$[M(p)m(L^1)n(L^2)o(L^3)p(L^4)q(L^5)r(L^6)s]t(D)u$$

wherein M is ruthenium or osmium; P is a polydentate ligand of M; $L^1, L^2, L^3, L^4, L^5$ and $L^6$ are ligands of M, each of which may be the same as or different from each other ligand; D is a substance covalently bound to one or more of P, $L^1, L^2, L^3, L^4, L^5, L^6$ through one or more amide or amine linkages; m is an integer equal to or greater than 1; each of n, o, p, q, r and s is zero or an integer; t is an integer equal to or greater than 1; u is an integer equal to or greater than 1; and P, $L^1, L^2, L^3, L^4, L^5, L^6$ and D are of such composition and number that the chemical moiety can be induced to emit electromagnetic radiation and the total number of bonds to M provided by the ligands of M equals the coordination number of M.

23. The method of claim 21 wherein the luminophore is selected from the group consisting of fluorescent or phosphorescent polyaromatic hydrocarbons and fluorescent or phosphorescent transition metal chelates.

24. A system for determining the time course of a biomolecular reaction comprising a first reagent mixture containing as reagents a reactant, a luminophore and a reaction partner wherein the reactant reacts with the reaction partner, and the luminophore participates with the reaction partner, or the reaction product of the reaction partner, to emit electrochemiluminescence upon exposure of the reagent mixture to electrical energy; a second reagent mixture having the components contained in the first reagent mixture except that it comprises reacted reagents; and a third reagent mixture having the components contained in the first reagent mixture except that it does not contain the reaction partner;

a means for separately exposing each of the first, second and third reagent mixtures to a series of electrical pulses at a preselected potential and at preselected intervals of time and duration; and a means for measuring the electrochemiluminescence at the preselected intervals of time.

25. The system of claim 24 wherein the reactant and the luminophore comprise a chemical moiety having the formula

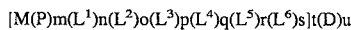

$$[M(P)m(L^1)n(L^2)o(L^3)p(L^4)q(L^5)r(L^6)s]t(D)u$$

wherein M is ruthenium or osmium; P is a polydentate ligand of M; $L^1, L^2, L^3, L^4, L^5$ and $L^6$ are ligands of M, each of which may be the same as or different from each other ligand; D is a substance covalently bound to one or more of P, $L^1, L^2, L^3, L^4, L^5$ or $L^6$ through one or more amide or amine linkages; m is an integer equal to or greater than 1; each of n, o, p, q, r and s is zero or an integer; t is an integer equal to or greater than 1; u is an integer equal to or greater than 1; and P, $L^1, L^2, L^3, L^4, L^5, L^6$ and D are of such composition and number that the chemical moiety can be induced to emit electromagnetic radiation and the total number of bonds to M provided by the ligands of M equals the coordination number of M.

26. The system of claim 24 wherein the luminophore is selected from the group consisting of fluorescent or phosphorescent polyaromatic hydrocarbons and fluorescent or phosphorescent transition metal chelates.

27. The system of claim 26 wherein the transition metal chelates are organometallic compounds.

28. The system of claim 24 wherein the luminophore is selected from the group consisting of Ru-containing and Os-containing compounds.

29. The system of claim 24 wherein the luminophore is ruthenium tris-bypyridine or osmium tris-bipyridine.

30. The system of claim 24 wherein the biomolecular reaction is an enzymatic reaction, the reagent mixture contains an enzyme and the reactant is a substrate on which the enzyme exerts catalytic action, and the reaction partner is a cofactor.

31. The system of claim 30 wherein the luminophore is selected from the group consisting of fluorescent or phosphorescent polyaromatic hydrocarbons and fluorescent or phosphorescent transition metal chelates.

32. The system of claim 31 wherein the enzyme is an oxide reductase.

33. The system of claim 32 wherein the oxido reductase is a dehydrogenase.

34. The system of claim 31 wherein the cofactor is a metal ion.

35. The system of claim 31 wherein the cofactor is a coenzyme.

36. The system of claim 35 wherein the coenzyme is in its oxidized form.

* * * * *